US008996428B2

(12) United States Patent
Baras et al.

(10) Patent No.: US 8,996,428 B2
(45) Date of Patent: Mar. 31, 2015

(54) PREDICTING DIAGNOSIS OF A PATIENT

(75) Inventors: Dorit Baras, Haifa (IL); Ariel Farkash, Shimshit (IL); Edward Vitkin, Nesher (IL)

(73) Assignee: International Business Machines Corporation, Armonk, NY (US)

( * ) Notice: Subject to any disclaimer, the term of this patent is extended or adjusted under 35 U.S.C. 154(b) by 294 days.

(21) Appl. No.: 13/351,243

(22) Filed: Jan. 17, 2012

(65) Prior Publication Data
US 2013/0185231 A1 Jul. 18, 2013

(51) Int. Cl.
G06F 15/18 (2006.01)
G06F 19/00 (2011.01)

(52) U.S. Cl.
CPC .......... *G06F 19/3437* (2013.01); *G06F 19/345* (2013.01)
USPC .......................................................... 706/12

(58) Field of Classification Search
None
See application file for complete search history.

(56) References Cited

U.S. PATENT DOCUMENTS

| | | | |
|---|---|---|---|
| 5,508,912 A | 4/1996 | Schneiderman | |
| 7,089,185 B2* | 8/2006 | Nefian | 704/256 |
| 8,224,640 B2* | 7/2012 | Sharma et al. | 703/19 |
| 2002/0091687 A1 | 7/2002 | Eglington | |
| 2003/0204415 A1 | 10/2003 | Knowlton | |
| 2010/0312798 A1* | 12/2010 | Dutta et al. | 707/780 |
| 2011/0173022 A1 | 7/2011 | Mayer et al. | |
| 2012/0166208 A1* | 6/2012 | Gillam et al. | 705/2 |
| 2012/0232930 A1* | 9/2012 | Schmidt et al. | 705/3 |
| 2013/0031232 A1* | 1/2013 | Clymer et al. | 709/223 |

OTHER PUBLICATIONS

Learning Patient-Specific Models From Clinical Data by Shyam Visweswaran MBBS, JIPMER, Pondicherry, 1987 MS (Physiology and Biophysics), University of Illinois at Urbana-Champaign, 1995.*
Kunio Doi, Ph.D., "Computer-Aided Diagnosis in Medical Imaging: Historical Review, Current Status and Future Potential", Computerized Medical Imaging and Graphics, vol. 31, Issues 4-5, pp. 198-211, Jun.-Jul. 2007.
D. N. Cooper and J. Schmidtke, "Diagnosis of genetic disease using recombinant DNA", Human Genetics, vol. 87, No. 5,pp. 519-560, 1991.
Hertzman et al., "Parkinson's disease: A case-control study of occupational and environmental risk factors", American Journal of Industrial Medicine, vol. 17, No. 3, pp. 349-355, 1990.
G. Anthony Gorry, "Strategies for computer-aided diagnosis", Mathematical Biosciences, vol. 2, Issues 3-4, pp. 293-318, May 1968.

* cited by examiner

*Primary Examiner* — Kakali Chaki
*Assistant Examiner* — Ababacar Seck

(57) ABSTRACT

Method, system, and computer program product are provided for predicting diagnosis of a patient performed by a computerized device. The method may include: modeling data from a group of successfully diagnosed patients, wherein the data is modeled as treatment paths of patients including referrals to medical practitioners; and predicting diagnosis for a current patient by comparing a treatment path of the current patient with the modeled treatment paths of successfully diagnosed patients, including calculating a probability of a given diagnosis from the modeled treatment paths. The method may include: defining a set of medical entities including medical practitioners to which a patient has been referred; and gathering treatment paths of successfully diagnosed patients, wherein the treatment path links medical entities in a directional route. Predicting diagnosis for a current patient may use the modeled data to calculate the probability of each model instance for each diagnosis and choosing the model instance of the diagnosis that maximizes the treatment path probability.

22 Claims, 6 Drawing Sheets

PREDICTING DIAGNOSIS OF A PATIENT

BACKGROUND

This invention relates to the field of predicting diagnosis of a patient. In particular, the invention relates to computer-aided diagnosis (CAD) for predicting diagnosis of a patient.

Current methods of computer-aided diagnosis (CAD) of a patient's condition involve a combination of different types of analyses performed on clinical, molecular (genomic, proteomic, metabolic, etc.) and environmental data. For complex cases, using these methods is currently not sufficient. Complex diseases can intuitively be described as cases where the patient is constantly referred and re-directed from one physician to another yet over a long period of time his illness fails to be diagnosed. Thus, in these cases, new methods for analyzing a patient's medical condition are needed.

BRIEF SUMMARY

According to a first aspect of the present invention there is provided a computer-implemented method for predicting diagnosis of a patient performed by a computerized device having a processor, comprising: modeling data from a group of successfully diagnosed patients, wherein the data is modeled as treatment paths of patients including referrals to medical practitioners; and predicting diagnosis for a current patient by comparing a treatment path of the current patient with the modeled treatment paths of successfully diagnosed patients, including calculating a probability of a given diagnosis from the modeled treatment paths.

According to a second aspect of the present invention there is provided a computer program product for predicting diagnosis of a patient, the computer program product comprising: a computer readable non-transitory storage medium having computer readable program code embodied therewith, the computer readable program code comprising: computer readable program code configured to: model data from a group of successfully diagnosed patients, wherein the data is modeled as treatment paths of patients including referrals to medical practitioners; and predict diagnosis for a current patient by comparing a treatment path of the current patient with the modeled treatment paths of successfully diagnosed patients, including calculating a probability of a given diagnosis from the modeled treatment paths.

According to a third aspect of the present invention there is provided a system for predicting diagnosis of a patient, comprising: a processor; a modeling component for modeling data from a group of successfully diagnosed patients, wherein the data is modeled as treatment paths of patients including referrals to medical practitioners; and a patient analysis component for predicting diagnosis for a current patient by comparing a treatment path of the current patient with the modeled treatment paths of successfully diagnosed patients, including calculating a probability of a given diagnosis from the modeled treatment paths.

BRIEF DESCRIPTION OF THE SEVERAL VIEWS OF THE DRAWINGS

The subject matter regarded as the invention is particularly pointed out and distinctly claimed in the concluding portion of the specification. The invention, both as to organization and method of operation, together with objects, features, and advantages thereof, may best be understood by reference to the following detailed description when read with the accompanying drawings in which:

Figure 1:
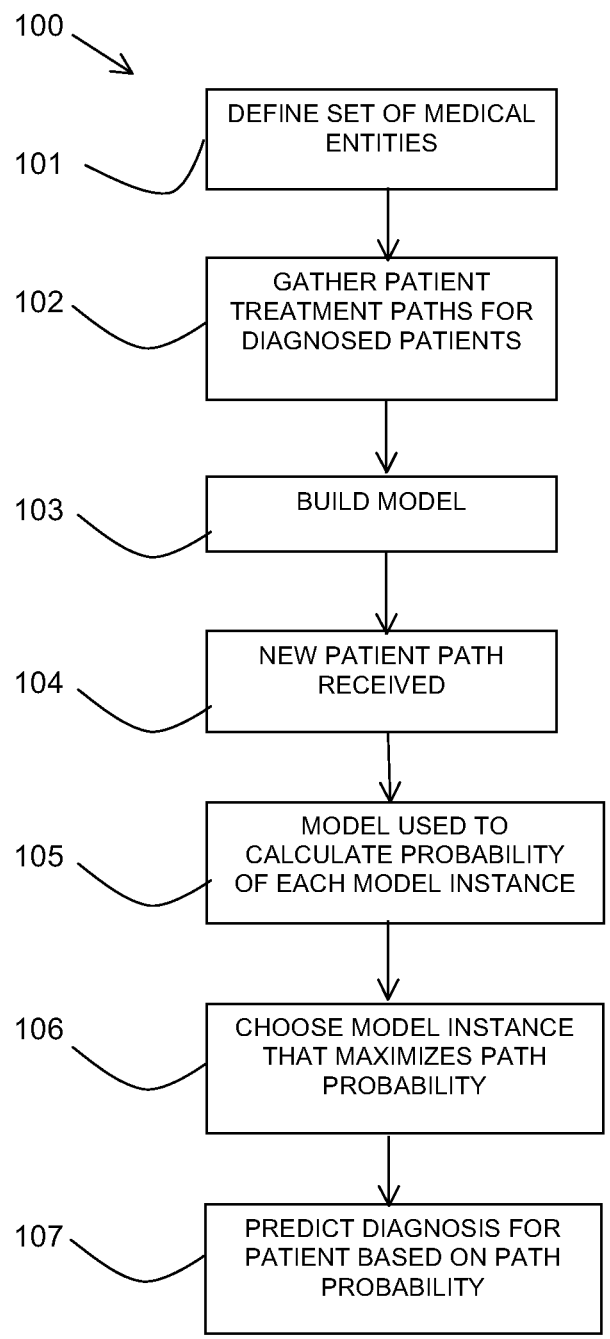
FIG. 1 is a flow diagram of a method in accordance with the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numbers may be repeated among the figures to indicate corresponding or analogous features.

DETAILED DESCRIPTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

Method, system and computer program product are described in which a patient's treatment path through the medical system is used as means for comparison between patients' conditions that can complement traditional methods based on clinical (and other) data.

The described solution is based on the assumption that physician treating patients may have an intuition regarding the patient's condition that is not always put to paper in a formal, machine-processable manner. Nevertheless, the referral of that patient by the physician for continuance of diagnosis and care is affected by this intuition and may serve as a means to capture this intuition and use it for comparison of the patient's condition and prediction of the patient's diagnosis based on available similar and successfully diagnosed cases. This may serve physicians as a decision support mechanism.

A method of predicting diagnosis for a patient is provided by comparing the treatment path of a patient with treatment paths of successfully diagnosed patients. A treatment path may be defined as a path through medical entities including different medical practitioners (wherein the term medical practitioner includes physician, specialists, and any other person providing tests, treatment, or therapy), referrals (even if not visited), tests, medications, intuition of physician regarding the condition of patient, solution to cure the condition of the patient, etc.

The method may include modeling a database with successfully diagnosed treatment paths. The method may then use the model to predict diagnosis for a patient by comparing the treatment path of the patient with the stored treatment paths, wherein the stored treatment paths are ranked based on order of similarity in the treatment path of the patient and the stored treatment paths.

A diagnosis of a patient may be of a single medical condition or of a combination of two or more medical conditions.

Referring to FIG. 1, a flow diagram 100 shows an embodiment of the described method. A set of medical entities may be defined 101 (manually or using clustering techniques). Patient treatment paths may be gathered 102 for as large a number of diagnosed patients as available. (For example, the paths may be gathered for all patients of a health maintenance organisation HMO with a positive diagnosis.) A model may then be built 103. An example implementation of a model build is given below. Given a new patient path 104, the model may be used to calculate 105 the probability of each model instance, and the model instance that maximizes the path probability may be chosen 106. A prediction of the diagnosis 107 of the patient may be made based on the path probability. A physician may use the received ranking according to path probabilities as decision support for advising further diagnosis.

An example implementation is described using Markov models combined with a Bayesian classifier. The method is composed of two different stages: a stage for learning the models and a stage of diagnosis prediction. The learning stage uses labeled patients' data (namely examples of paths of patients who were eventually diagnosed) to build a Markov model over the existing nodes of the paths. Model building and learning can be performed off-line and updated on a regular basis as more labeled data is available. The prediction stage uses a Bayesian classifier over the learned models to predict the diagnosis.

Figure 2:
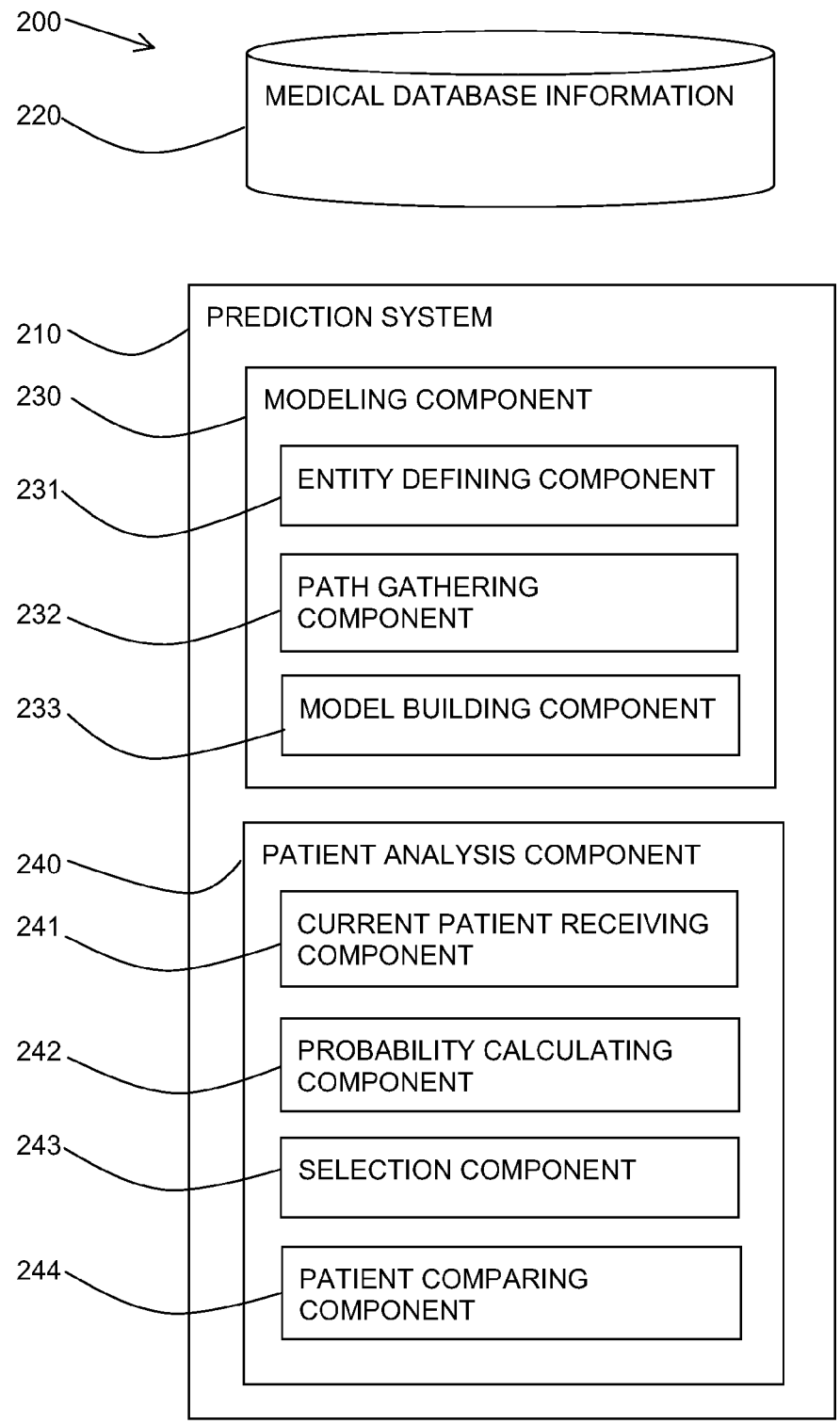
FIG. 2 is a block diagram of a system in accordance with the present invention.

Referring to FIG. 2, an embodiment of the described system 200 is shown in a block diagram. A prediction system 210 is provided for predicting a patient's diagnosis based on medical database information 220. The medical database information may be provided from multiple sources.

The predication system 210 may include two components: a modeling component 230 for modeling successfully diagnosed patient records; and a patient analysis component 240 for applying the models to a current patient.

The modeling component 230 may include an entity defining component 231 which may use manual or clustering techniques. The modeling component 230 may also include a path gathering component 232 for gathering treatment paths of diagnosed patients as retrieved from medical database information 220. The modeling component 230 may also include a model building component 233 for building probability models based on the paths of diagnosed patients.

The patient analysis component 240 may include a current patient receiving component 241 for receiving path information for a current patient for which diagnosis is required. The patient analysis component 240 may include a probability calculating component 242 for calculating the probability of each model instance. The patient analysis component 240 may also include a selection component 243 for selecting a maximum probability diagnosis. The patient analysis component 240 may include a patient comparing component 244 for comparing two or more patients given multiple diagnosis models.

Figure 3:
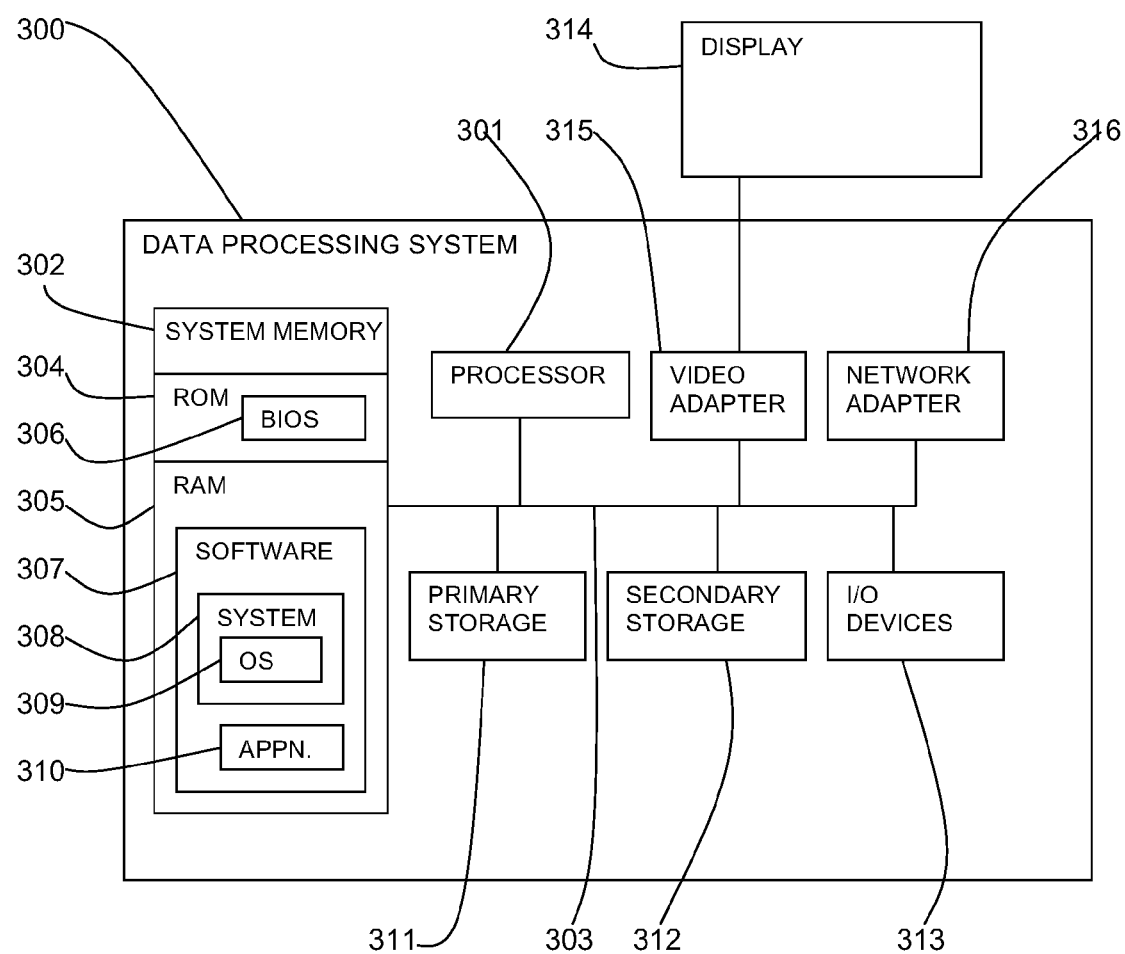
FIG. 3 is a block diagram of a computer system in which the present invention may be implemented.

Referring to FIG. 3, an exemplary system for implementing aspects of the invention includes a data processing system 300 suitable for storing and/or executing program code including at least one processor 301 coupled directly or indirectly to memory elements through a bus system 303. The memory elements can include local memory employed during actual execution of the program code, bulk storage, and cache memories which provide temporary storage of at least some program code in order to reduce the number of times code must be retrieved from bulk storage during execution.

The memory elements may include system memory 302 in the form of read only memory (ROM) 304 and random access memory (RAM) 305. A basic input/output system (BIOS) 306 may be stored in ROM 304. System software 307 may be stored in RAM 305 including operating system software 308. Software applications 310 may also be stored in RAM 305.

The system 300 may also include a primary storage means 311 such as a magnetic hard disk drive and secondary storage means 312 such as a magnetic disc drive and an optical disc drive. The drives and their associated computer-readable media provide non-volatile storage of computer-executable instructions, data structures, program modules and other data for the system 300. Software applications may be stored on the primary and secondary storage means 311, 312 as well as the system memory 302.

The computing system 300 may operate in a networked environment using logical connections to one or more remote computers via a network adapter 316.

Input/output devices 313 can be coupled to the system either directly or through intervening I/O controllers. A user may enter commands and information into the system 300 through input devices such as a keyboard, pointing device, or other input devices (for example, microphone, joy stick, game pad, satellite dish, scanner, or the like). Output devices may include speakers, printers, etc. A display device 314 is also connected to system bus 303 via an interface, such as video adapter 315.

Specific Possible Model Implementation—Usage of Markov Chains

A model may be built as follows: stations along the path represent a medical entity (Doctors with certain specialization, certain types of medical exams, etc.). These stations are referred to as nodes. The nodes can be either pre-determined, or automatically clustered to create these entities. A path is a list of entities that a certain patient visited. Each path in the training set is labeled with a single diagnosis. Each entity is given a unique ID (for example, E1, E2, . . . , EN), and each diagnosis is also given a unique ID (for example d1, d2, . . . , dM). A learning example is composed of a path (list of entities, for example: E4, E7, E13, E2, E4, E12) and a diagnosis label (for example D23). Note that a path can be recurrent in that a certain entity can be visited more than once.

A different Markov model instance (Markov chain) is learnt for each diagnosis (wherein a diagnosis may be of a single medical condition or a combination of medical conditions). The model instance consists of transition probabilities between each pair of nodes. For diagnosis dk we learn a Markov model instance over E1, ..., En, namely P(ij)=Prob (x(n+1)=Ei|x(n)=Ej), where (i;j)=(1, ..., N). These probabilities can be learned using ML (Maximum-Likelihood) estimation as follows: P(ij)=(#transactions from Ei to Ej)/ (#transactions from Ei to any node). Another option is using MAP (Maximum a-Posteriori) estimation which also incorporates the a-priori probability of being in any node Ei (that can be given by an expert).

Prediction Stage

Given the learned model instances and a current path of an undiagnosed patient, a simple naïve Bayes classifier may be used to predict the diagnosis. For each of the diagnoses (model instances), Prob(dk|path) is calculated as follows:

$$P(\text{Diagnosis} = D_i \mid \text{Path}) = \frac{P(\text{Path} \mid D_i)P(D_i)}{P(\text{Path})}$$
$$= \frac{P(\text{Path} \mid D_i)P(D_i)}{\sum_j P(\text{Path} \mid D_j)P(D_j)}$$

Prob(Path|model) may be calculated from the model instance as follows:
$P(\text{Path}|D_i) = \Pi_{n-1}^{T} P(E(n)|E(n-1))$, where T is the path length and $P(E(1)|E(0))=P(E(1))$ is defined by an expert.

P(D) may be calculated either using expert knowledge or using a maximum likelihood estimator, for example:
P(D)=#labelled samples with diagnosis D/#total number of labelled samples.

The physician can either take the diagnosis that maximizes the probability, or sort the probabilities, and obtain a rank of the likelihood of each diagnosis.

Similarity of Patient Paths

The described method can may also be used to find similarities between a pair of patients based on the similarities of their paths and the given diagnosis models. An example of a simple algorithm that may perform such a comparison is as follows. Consider two patients, A and B, and several diagnosis Markov chains, d_1, d_2, ..., d_k. For both patients, calculate the probabilities of paths being drawn from each diagnosis, and result with two vectors containing those probabilities: {P(A|d_1), P(A|d_2), ..., P(A|D_k)} and {P(B|d_1), P(B|d_2), ..., P(B|D_k)}. The two vectors may be compared (using mutual information metric or Euclidean distance) and a distance between patients A and B obtained.

Detailed Example:

Any number of clustering methods may be used to define the medical entities.

Patient treatment graphs may be gathered for numerous patients. A patient treatment graph may be based on patient treatment history. It will be a directed graph with several entry nodes. Each node represents a medical entity or treatment stage. Each arrow represents dependency of the current stage with previous stage. Node numbers identify treatment stages ordered by the time they happen. Unvisited nodes have no number. Node letters identify treatment types. At each stage, a patient may go to one of the already visited nodes or to a new, independent entry node.

A method of graph building is explained by the next example.

Patient's Story

Figure 4A:
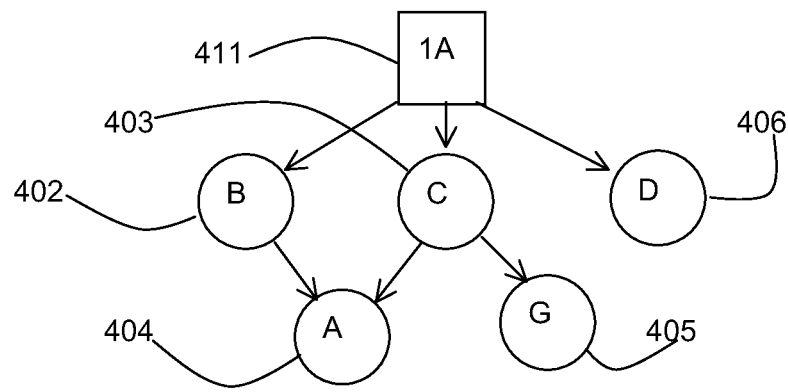
FIGS. 4A to 4C are schematic diagrams illustrating an example case in accordance with the present invention.
Figure 4B:
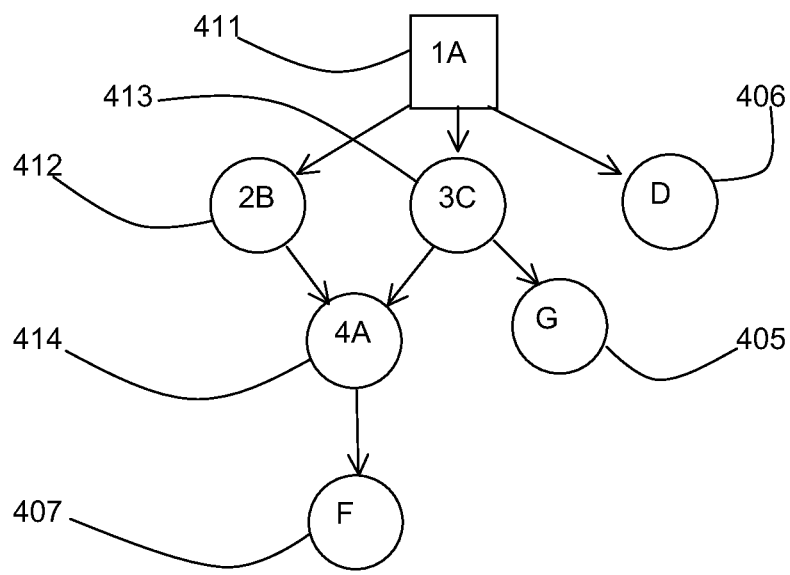
Figure 4C:
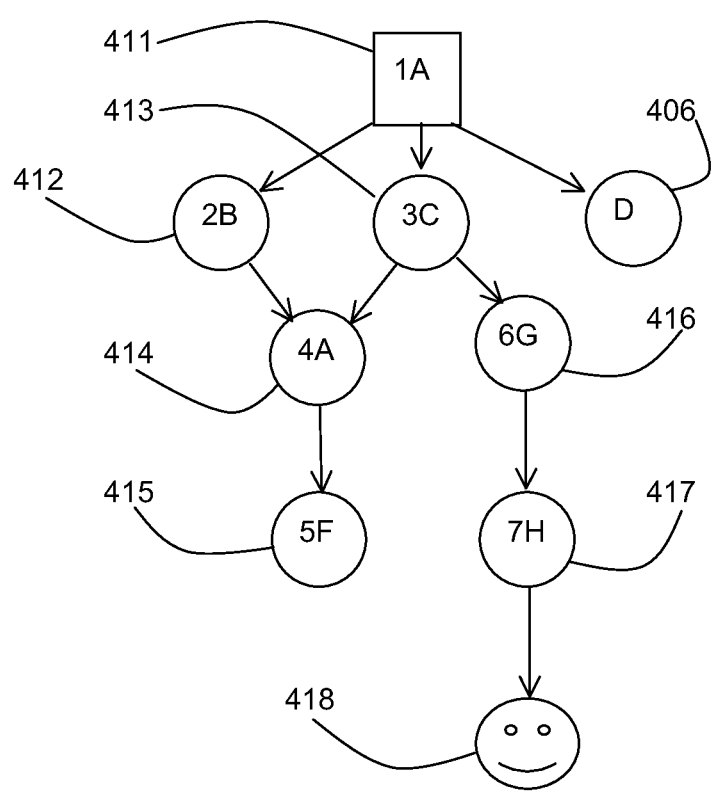

Referring to FIGS. 4A to 4C, an example case is represented by schematic diagrams showing a patient's path or graph through medical entities.

Referring to FIG. 4A, the patient, John, came (step 1A 411) to his family doctor (A) Ann with headaches.

Ann said that it can be caused by neurological problems and opens for John an appointment to couple blood test (B 402) and to motoric reactions test (C 403). After the completion of both tests, she wants to see John again (A 404) and after the completion of motoric test (C 403) she wants John to visit a neurologist (G 405).

Moreover, there is a chance that the problem is caused by dental issues, so Ann opens an appointment to a dentist (D 406). Since John is really afraid of dentists, he decides to do the other tests first.

Referring to FIG. 4B, John goes to the blood test (step 2B 412) and then does the motoric test (step 3C 413). After that he visits Ann again (step 4A 414) and she proposes him some antivirus treatment (F 407).

Referring to FIG. 4C, John uses the antivirus pills (step 5F 415), but they do not help, so he decides to go to neurologist (step 6G 416). The neurologist makes a diagnosis of migraines and gives to John the appropriate treatment (H). After John uses the treatment (step 7H 417) he feels well 418, so the case ends here.

FIG. 4C shows the final patient treatment process graph. There is a single entry node 411, represented by rectangle and single final node 418, here represented by a "smiley", since the case was solved. Although steps 1A 411 and 4A 414 are visits to the same doctor, they are different, since the information available to the doctor at the two stages is different.

The order of visited nodes may be defined as a patient treatment path. In this case, it is (1A,2B,3C,4A,5F,6G,7H). This path may now used to build the model in the next stage.

Building of the Markov Model

Figure 5:
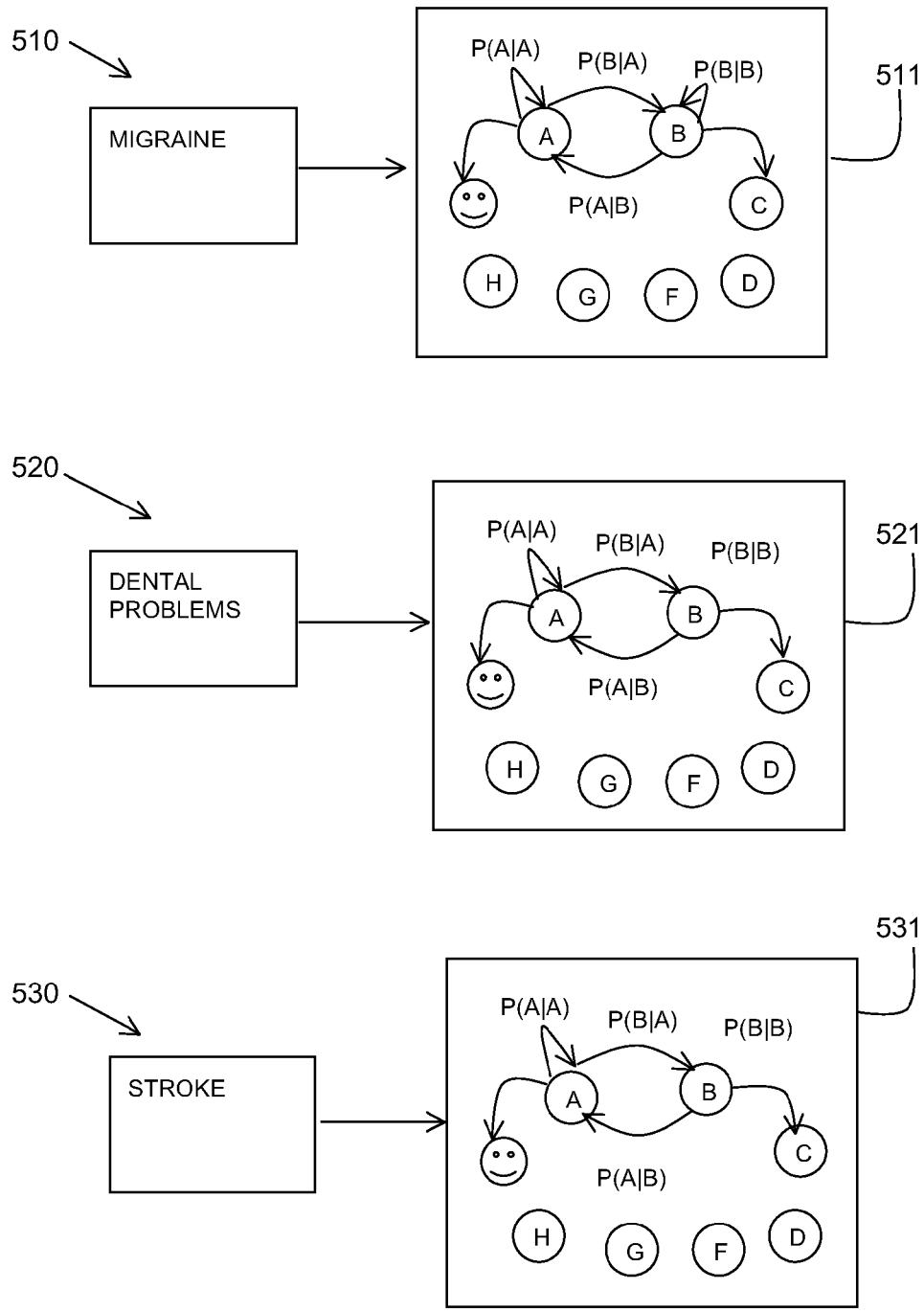
FIG. 5 is a schematic diagram illustrating models in accordance with the present invention.

Referring to FIG. 5, based on a database of similar cases, three possible diagnoses 510, 520, 530 are shown based on constructed model instances 511, 521, 531 with the model instances having calculated probabilities for each step between medical entities in the model paths.

Models may be directed cliques and, in theory, there may be a directed edge between every pair of edges. In the illustrated example, most of the edges are omitted and only a small fraction of them are presented. The model instances differ in the exact values of the probabilities.

A new and unsolved case is now presented as an example. For example, a patient may have a path similar to John, for example, path (1A,2B,3C,4A,5F,6G). The probabilities of all possible diagnoses are calculated based on this path.
P(Migraine)=0.3
P(Dental Problems)=0.001
...
P(Stroke)=0

The probability of each diagnosis is calculated from multiplication of the arrows shown in each of the model instances 511, 512, 513 of FIG. 5.

A physician may receive the resultant probabilities sorted according to their value. This may then be used to diagnose the patient.

An additional application may be deciding the best possible alternative for a continued treatment path. In the example, it would mean providing a prescription for a treatment state for Migraine (H). This is done by taking the next node with highest probability from G in the model.

A patient diagnosis prediction system may be provided as a service to a customer over a network.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

What is claimed is:

1. A computer-implemented method for predicting diagnosis of a patient performed by a computerized device having a processor, comprising:
   modeling data from a group of patients successfully diagnosed as having one or more medical conditions, wherein the data is modeled as treatment paths of patients including referrals to medical practitioners; and
   predicting diagnosis of one or more medical conditions for a current patient by comparing a treatment path of the current patient with the modeled treatment paths of successfully diagnosed patients, including calculating a probability of a given diagnosis of one or more medical conditions from the modeled treatment paths, wherein the calculating is in accordance with:

$$\frac{P(\text{Path}|D_i)P(D_i)}{P(\text{Path})}$$

where:
P denotes probability,
Path denotes the treatment path of the current patient, and
$D_i$ denotes the given diagnosis.

2. The method as claimed in claim 1, wherein modeling data includes:
defining a set of medical entities including medical practitioners to which a patient has been referred; and
gathering treatment paths of successfully diagnosed patients, wherein the treatment path links medical entities in a directional route.

3. The method as claimed in claim 2, wherein the medical entities include one or more of the group of: medical practitioners visited; medical practitioners referred to; tests carried out or recommended; medications prescribed; therapies carried out or recommended; diagnosis.

4. The method as claimed in claim 2, wherein the medical entities are defined by manual or automated clustering techniques.

5. The method as claimed in claim 1, wherein modeling data models the treatment paths of successfully diagnosed patients using a different Markov model instance for each possible diagnosis.

6. The method as claimed in claim 5, wherein the Markov model instances include transition probabilities between medical entities learned using probability estimation techniques.

7. The method as claimed in claim 1, wherein modeling data is carried out off-line and regularly updated.

8. The method as claimed in claim 1, wherein predicting diagnosis for a current patient uses the modeled data to calculate the probability of each model instance for each diagnosis and choosing the model instance of the diagnosis that maximizes the treatment path probability.

9. The method as claimed in claim 6, wherein predicting diagnosis includes using a Bayesian classifier to predict a given diagnosis given the Markov model instances and a current path.

10. The method as claimed in claim 1, including sorting the possible diagnosis by the probability of each possible diagnosis.

11. The method as claimed in claim 1, including:
given two or more patients and multiple diagnosis models;
for each patient calculating the probability vectors of paths for one or more diagnoses; and
comparing the probability vectors for the patients to determine similarities.

12. A computer program product for predicting diagnosis of a patient, the computer program product comprising a non-transitory computer readable storage medium having computer readable program code embodied therewith, the computer readable program code executable by at least one processor to:
model data from a group of patients successfully diagnosed as having one or more medical conditions, wherein the data is modeled as treatment paths of patients including referrals to medical practitioners; and
predict diagnosis of one or more medical conditions for a current patient by comparing a treatment path of the current patient with the modeled treatment paths of successfully diagnosed patients, including calculating a probability of a given diagnosis of one or more medical conditions from the modeled treatment paths, wherein the calculating is in accordance with:

$$\frac{P(\text{Path}|D_i)P(D_i)}{P(\text{Path})}$$

where:
P denotes probability,
Path denotes the treatment path of the current patient, and
$D_i$ denotes the given diagnosis.

13. A system for predicting diagnosis of a patient, comprising:
a processor;
a modeling component for modeling data from a group of patients successfully diagnosed as having one or more medical conditions, wherein the data is modeled as treatment paths of patients including referrals to medical practitioners; and
a patient analysis component for predicting diagnosis of one or more medical conditions for a current patient by comparing a treatment path of the current patient with the modeled treatment paths of successfully diagnosed patients, including calculating a probability of a given diagnosis of one or more medical conditions from the modeled treatment paths, wherein the calculating is in accordance with:

$$\frac{P(\text{Path}|D_i)P(D_i)}{P(\text{Path})}$$

where:
P denotes probability,
Path denotes the treatment path of the current patient, and
$D_i$ denotes the given diagnosis.

14. The system as claimed in claim 13, wherein the modeling component includes:
an entity defining component for defining a set of medical entities including medical practitioners to which a patient has been referred; and
a path gathering component for gathering treatment paths of successfully diagnosed patients, wherein the treatment path links medical entities in a directional route.

15. The system as claimed in claim 14, wherein the entity defining component is for defining medical entities by manual or automated clustering techniques.

16. The system as claimed in claim 13, wherein the modeling component includes:
a model building component for modeling the treatment paths of successfully diagnosed patients using a different Markov model instance for each diagnosis.

17. The system as claimed in claim 16, wherein the Markov model instances include transition probabilities between medical entities learned using probability estimation techniques.

18. The system as claimed in claim 13, wherein the modeling component operates off-line and regularly updated.

19. The system as claimed in claim 13, wherein the patient analysis component includes:
a current patient receiving component for receiving a current patient treatment path;
a probability calculating component for using the modeled data to calculate the probability of each model instance for each possible diagnosis; and
a selection component for choosing the model instance of the diagnosis that maximizes the treatment path probability.

20. The system as claimed in claim 16, wherein the probability calculating component includes a Bayesian classifier to predict a given diagnosis given the Markov model instances and a current path.

21. The system as claimed in claim 19, wherein the selection component includes a ranking component for sorting the possible diagnosis by the probability of each possible diagnosis.

22. The system as claimed in claim 13, including a patient comparing component for comparing two or more patients given multiple diagnosis models, including:
- for each patient calculating the probability vectors of paths for one or more diagnoses; and
- comparing the probability vectors for the patients to determine similarities.

\* \* \* \* \*